(12) United States Patent
Bertels

(10) Patent No.: US 6,736,855 B2
(45) Date of Patent: May 18, 2004

(54) TRACTION BANDAGE

(75) Inventor: Thomas Bertels, Dudersstadt (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 28 days.

(21) Appl. No.: 10/185,736

(22) Filed: Jul. 1, 2002

(65) Prior Publication Data

US 2003/0004447 A1 Jan. 2, 2003

(30) Foreign Application Priority Data

Jul. 2, 2001 (DE) .................................. 201 10 727 U

(51) Int. Cl.[7] .................................................. A61F 2/66
(52) U.S. Cl. ............................. 623/57; 623/58; 623/59; 623/60; 623/61; 623/62; 623/63; 623/64; 623/65; 623/30; 623/31; 623/32
(58) Field of Search ............................... 623/57–65, 30, 623/31, 32; 2/44, 45, 305, 309, 319; D2/330

(56) References Cited

U.S. PATENT DOCUMENTS

| | | | | | |
|---|---|---|---|---|---|
| 483,090 A | * | 9/1892 | Wortham | .................... | 623/58 |
| 598,452 A | * | 2/1898 | Tullis | .................... | 623/30 |
| 776,908 A | * | 12/1904 | Henry | .................... | 623/35 |
| 1,046,966 A | * | 12/1912 | Carnes | .................... | 623/62 |
| 1,216,367 A | * | 2/1917 | Rowley | .................... | 623/33 |
| 4,258,441 A | * | 3/1981 | Bell | .................... | 623/64 |
| 4,268,922 A | * | 5/1981 | Marsh et al. | .................. | 623/38 |
| 5,116,386 A | * | 5/1992 | Scribner | ....................... | 623/64 |
| 5,651,792 A | * | 7/1997 | Telikicherla | .................. | 623/36 |

* cited by examiner

Primary Examiner—Corrine McDermott
Assistant Examiner—Alvin Stewart
(74) Attorney, Agent, or Firm—Whitham, Curtis & Christofferson, PC

(57) ABSTRACT

A bandage which may be used for the forearm or as an upper arm triple traction bandage includes a bandage strap (3) that engages a ring (2) to form a loop. At least one elastic bandage strap (4) engages the ring (2) and encloses a cable (6) which at one end is secured to the ring (2) and has a fastening device at its other end (4a). The fastening device is formed by a strap connector (11, 12, 13) having a flat lower part (11) which is adapted to the strap width. The upper side is covered by a flat upper part (12) onto which a clamp slide (13) is pushed that engages under the lower part (11) and firmly presses the lower part and upper part together with the strap end (4a) lying between them. The strap connector (11, 12, 13) has a clamp-free cable passage (14, 15, 16) and a bracket (19) for securing the strap connector (11, 12, 13) to a prosthesis part.

14 Claims, 4 Drawing Sheets

TRACTION BANDAGE

The invention relates to a bandage, e.g. forearm bandage or upper arm triple traction bandage, with a first bandage strap engaging on a ring and forming a loop or similar, and with at least one second elastic bandage strap which likewise engages on the ring and encloses a cable which at one end is secured on the ring and at its other end is acted upon by a Bowden wire or similar, and can be fixed with its free strap end on a prosthesis part via a fastening device.

The object of the invention is to improve the handling and function of such a bandage.

Starting from the bandage described above, this object is achieved, according to the invention, by the fact that the fastening device is formed by a strap connector having a flat lower part which is adapted to the strap width and on which said strap end bears, which on its upper side is covered by a likewise flat upper part onto which a clamp slide is pushed which also engages under the lower part and firmly presses the lower part and upper part together with the strap end lying between them, the strap connector having a clamp-free cable passage and a bracket for securing the strap connector to a prosthesis part.

It is expedient if the ring for securing the cable has at least one radial bore which has, on the ring inner side, a recess of greater diameter into which there engages a sleeve screwed onto the cable end.

Further features of the invention are the subject of the subclaims and are explained in greater detail, together with further advantages of the invention, using illustrative embodiments.

Two embodiments of the invention which will serve as examples are shown in the drawing, in which.

Figure 1:
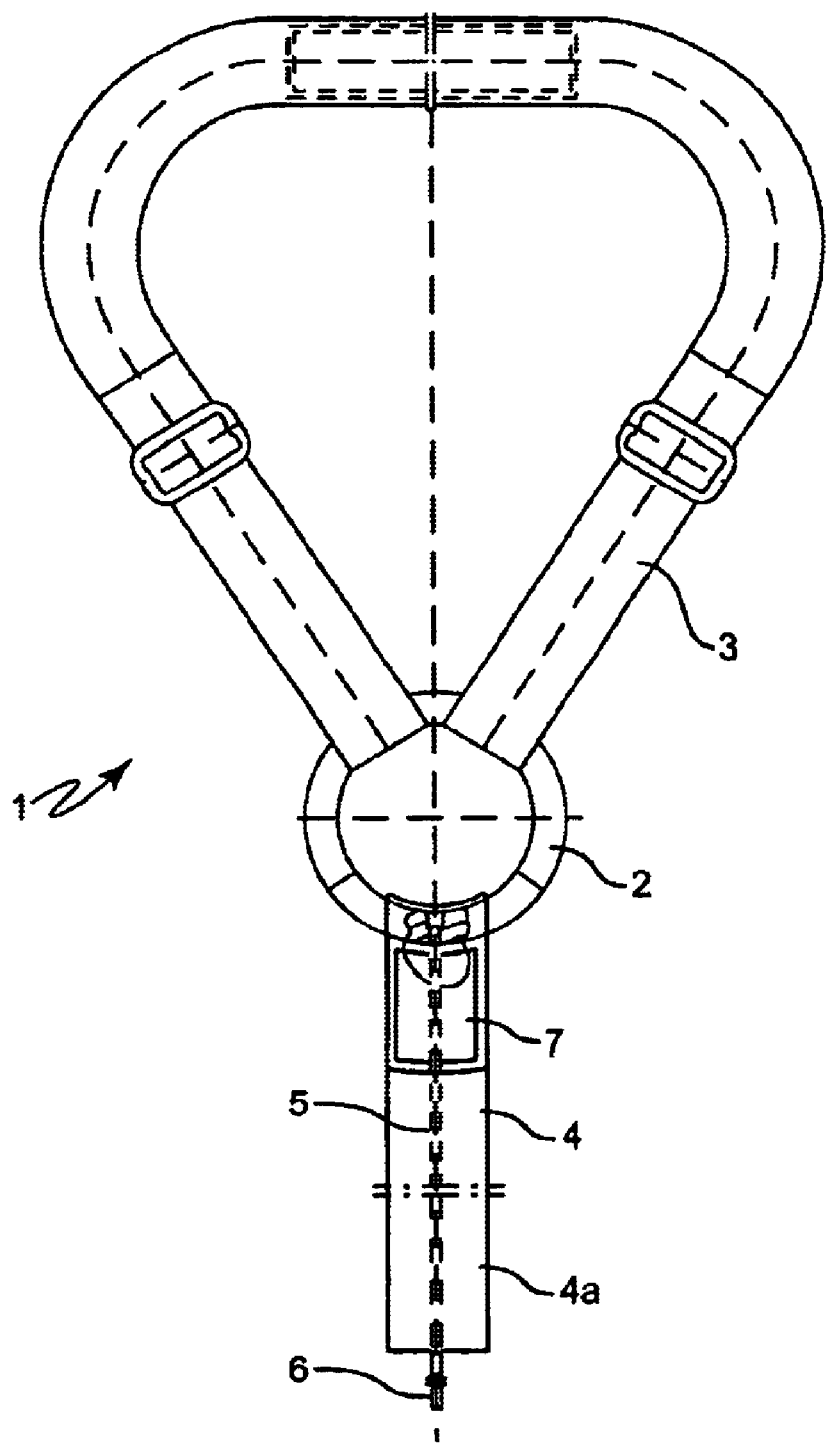
FIG. 1 shows a plan view of a forearm bandage.

FIG. 1 shows a forearm bandage 1 with a first bandage strap 3 engaging on a ring 2 and forming a loop, and with a second bandage strap 4 which likewise engages on the ring 2, is made elastic and has a through-channel 5 in which a cable 6 formed by a Perlon wire is guided. The elastic bandage strap 4 is secured at one end via a connection bracket 7 guided round the ring 2. For securing the cable 6, the ring 2 has a radial bore 8 which has, on the ring inner side, a recess 8a of greater diameter into which there engages a sleeve 9 screwed onto that end of the cable 6 which is guided through the radial bore 8. The radial bore 8 thus serves for fixing and positioning the cable required for the traction bandage.

Figure 2:
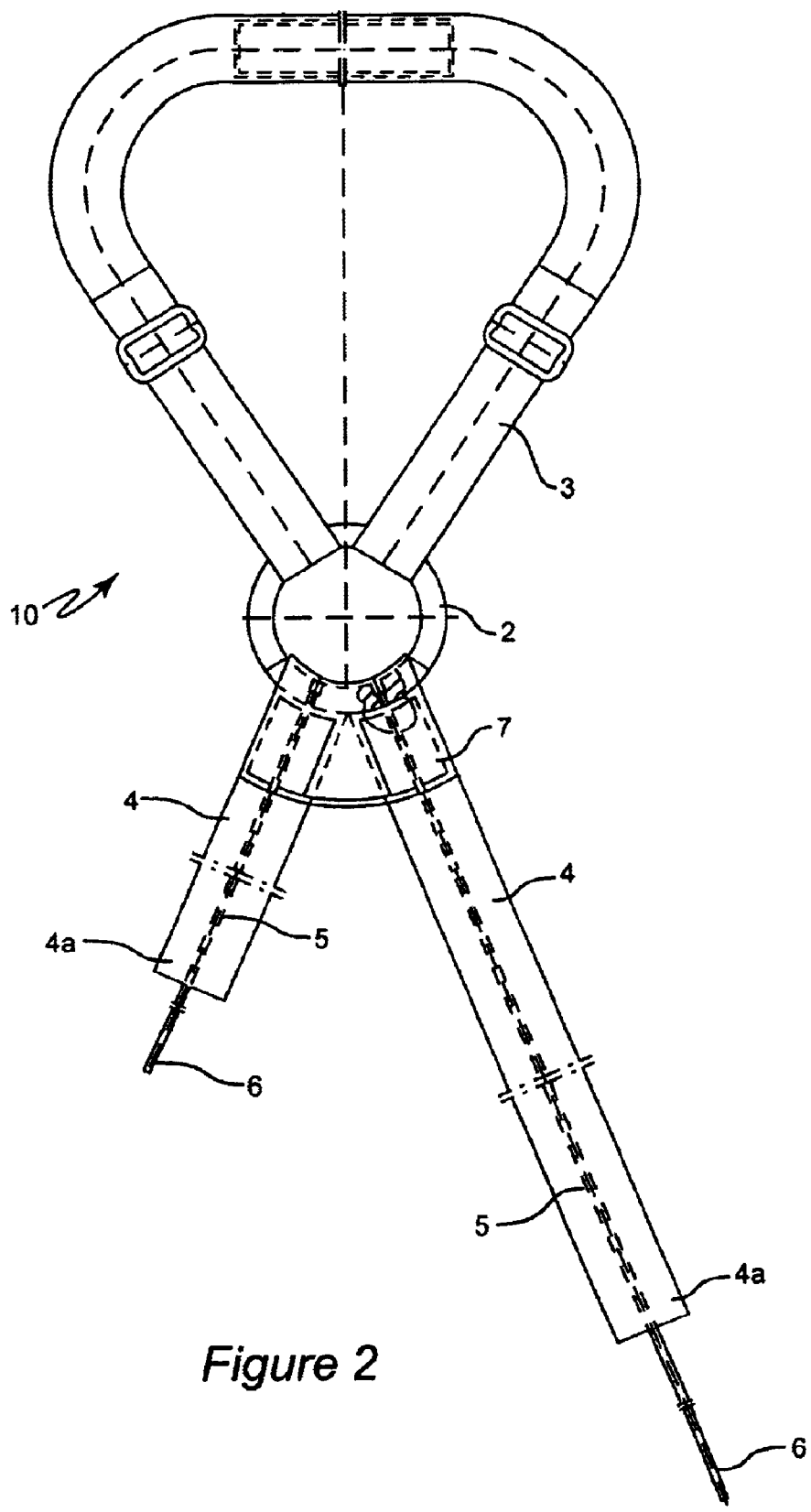
FIG. 2 shows an upper arm triple traction bandage in a view according to FIG. 1.

FIG. 2 shows an upper arm triple traction bandage 10 on whose ring 2 there engage two elastic bandage straps 4. These two elastic bandage straps 4 are secured on the ring 2, and the cable 6 provided in each of these two bandage straps is fixed on the ring 4, in the manner described above. So that the ring 2 can be used both for forearm bandages 1 and also for upper arm triple traction bandages 10, it has from the outset three radial bores 8 which are each provided with a recess 8a. By securing the cables 6 in the radial bores 8, the elastic bandage straps 4 are always held in a defined position and cannot slip on the ring 2. The way in which the cables 6 and the elastic bandage strap or straps 4 are secured on the ring 2 affords the possibility of designing the ring 2 with a flat elliptic cross section. The ring 2 therefore has a low overall height and does not therefore extend so far out on the back of the person wearing the bandage. However, the ring 2 is easily able to take up the forces acting on it.

Figure 3:
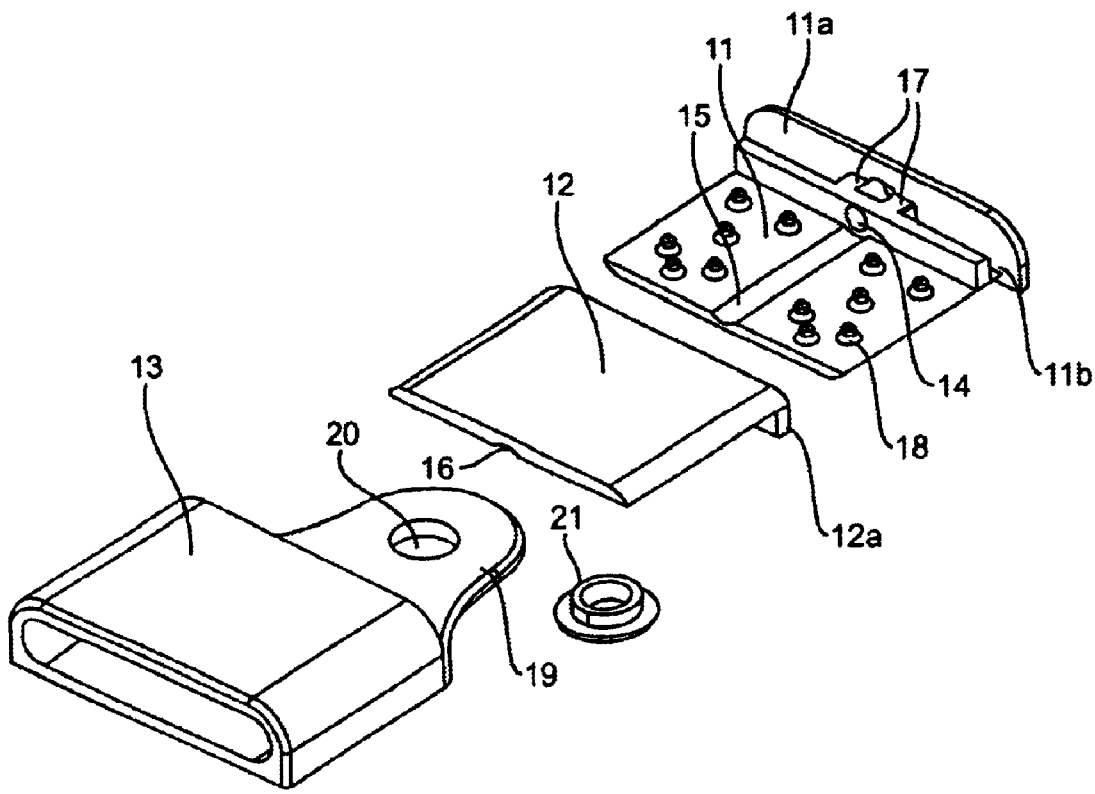
FIG. 3 shows, in an exploded view, a strap connector consisting of an upper part, a lower part, a clamp slide and a spacer sleeve.
Figure 4:
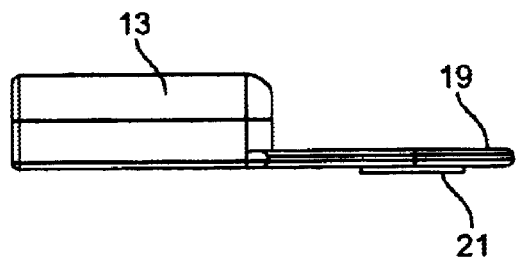
FIG. 4 shows the clamp slide according to FIG. 3 in a side view.
Figure 5:
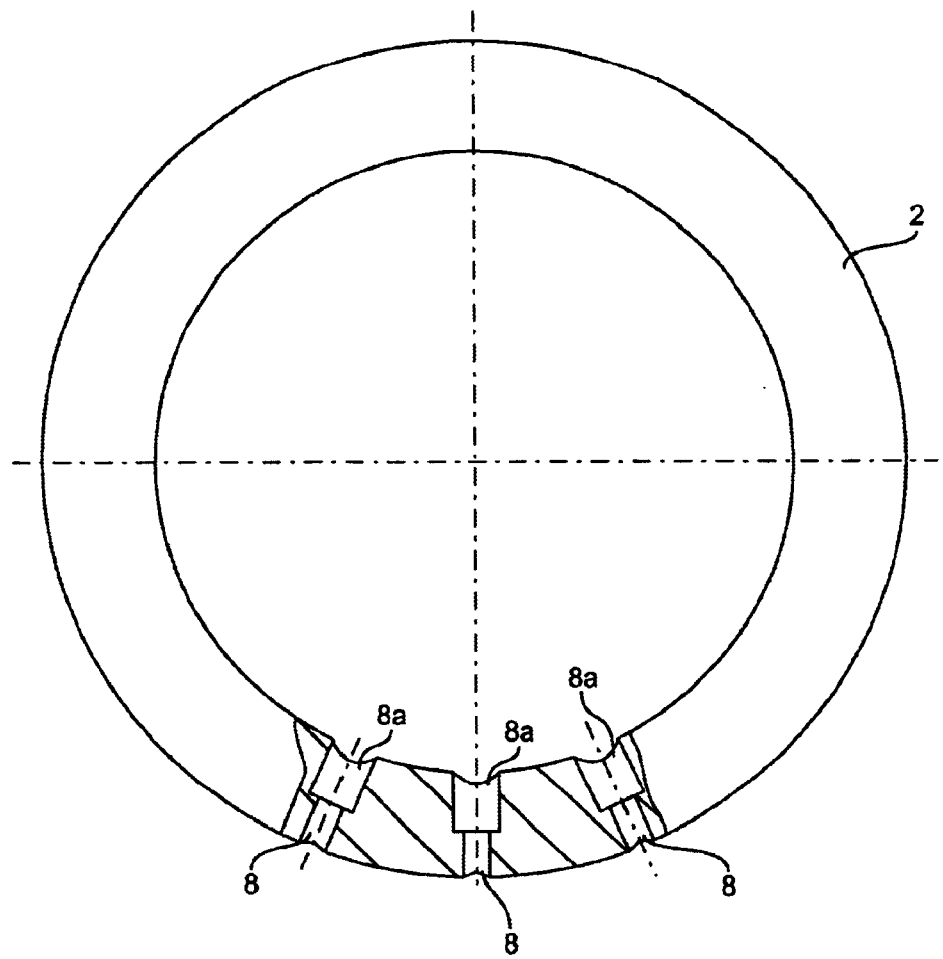
FIG. 5 shows a ring, represented in FIGS. 1 and 2, on an enlarged scale and partly in longitudinal section.
Figure 6:
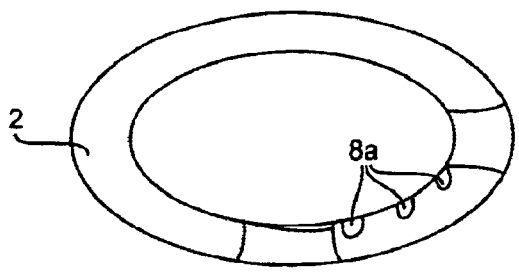
FIG. 6 shows the ring according to FIG. 5 in a somewhat perspective view.

The free strap end 4a of the elastic bandage strap 4 shown in FIGS. 1 and 2 is secured to a prosthesis part (not shown in the drawing); the free end of the cable 6 is acted upon by a Bowden wire or similar (likewise not shown in the drawing). For securing the strap end 4a, a strap connector is provided whose details are shown in FIG. 3 and whose side view is shown in FIG. 4. Accordingly, the strap connector comprises a flat lower part 11 which is adapted to the strap width and on which the free strap end 4a bears, which on its upper side is covered by a likewise flat upper part 12 onto which a clamp slide 13 is pushed which also engages under the lower part 11 and firmly presses the lower part 11 and upper part 12 together with the strap end 4a lying between them. The clamp slide 13 is designed as a closed sleeve having a flat cross section, as can be seen from FIG. 3. The lower part 11 has, at its front transverse edge directed toward the free strap end 4a, a transverse web 11a serving as displacement limit stop for the clamp slide 13, which is pushed onto lower part and upper part 11, 12 into its clamping position in a direction away from the ring 2.

A clamp-free cable passage is formed in the strap connector. For this purpose, a bore 14 is provided in the transverse web 11a of the lower part 11 to permit the passage of the cable 6, said bore 14 being flush with a groove 15, 16 provided both in the lower part 11 and in the upper part 12 of the strap connector.

In order to ensure an exact fixing of upper part and lower part 11, 12 and to ensure that the traction forces acting on the upper part 12 are introduced into the lower part 11, the upper part 12 engages with a folded edge 12a in a slit 11b of the transverse web 11a of the lower part 11 and engages, via a corresponding recess in the folded edge 12a, over fixing lugs 17 which are provided on both sides of said bore 14 and which interrupt the slit 11b.

To support the frictional clamping connection of the strap end 4a between the lower part 11 and the upper part 12 of the strap connector, the surfaces of the lower part and upper part bearing on the strap end 4a are in each case provided with pin-shaped elevations 18.

The clamp slide 13, bearing in its pushed-on clamping position on the transverse web 11a of the lower part 11, has a bracket 19 via which the strap connector is intended to be fastened in a pivotable manner to the prosthesis part (not shown). For this purpose, the bracket 19 is provided with a bore 20 which is provided with a spacer sleeve 21 which ensures that the strap connector can turn freely on the prosthesis shaft and thus adapt to every movement. The bracket 19 is designed in such a way that, when screwed on, it adapts to the contour of the prosthesis shaft.

What is claimed is:

1. A bandage having first bandage strap engaging on a ring and forming a loop or similar, and at least one second elastic bandage strap which engages on the ring and encloses a cable which at one end is secured on the ring and at its other end is acted upon by a Bowden wire or similar, and can be fixed with its free strap end on a prosthesis part via a fastening device, comprising:

a fastening device formed by a strap connector having a flat lower part which is adapted to the strap width and on which said strap end (4a) bears, said fastening device on its upper side is covered by a flat upper part onto which a clamp slide is pushed, said clamp slide engages under the lower part and firmly presses the lower part and upper part together with the strap end lying between them, said strap connector having a clamp-free cable passage and a bracket for securing the strap connector to a prosthesis part.

2. Bandage according to claim 1, wherein the clamp slide is a closed sleeve having a flat cross-section.

3. Bandage according to claim 1, characterized in that the clamp slide is pushed onto the lower part and upper part into its clamping position in a direction away from the ring.

4. Bandage according to claim 1, characterized in that the lower part has, at its front transverse edge directed toward the free strap end, a transverse web service as displacement limit stop for the clamp slide.

5. Bandage according to claim 4, characterized in that the transverse web has a bore for the clamp-free cable passage.

6. Bandage according to claim 5, characterized in that a groove for the clamp-free cable passage is provided in the lower part and/or upper part of the strap connector.

7. Bandage according to claim 4, characterized in that the upper part engages with a folded edge in a slit of the transverse web.

8. Bandage according to claim 7, characterized in that the slit is interrupted on both sides of said bore by fixing lags which engage in a corresponding recess in the folded edge of the upper part.

9. Bandage according to claim 1, characterized in that the surface of the lower part and upper part of the strap connector bearing on the strap end are provided with pin-shaped elevations.

10. Bandage according to claim 1, characterized in that said bracket has a bore which is provided with a spacer sleeve.

11. Bandage according to claim 1, characterized in that said cable is a Perlon wire.

12. Bandages according to claim 1, characterized in that the elastic bandage strap has a channel in which the cable is guided.

13. Bandage according to claim 1, characterized I that the ring has a flat elliptic cross section.

14. Bandage according to claim 1, characterized in that the ring for securing the cable has at least one radial bore which has, on the ring inner side, a recess of greater diameter into which there engages a sleeve screwed onto the cable end.

* * * * *